| United States Patent [19] | [11] 3,988,475 |
|---|---|
| Manghisi et al. | [45] Oct. 26, 1976 |

[54] PHENOXYALKYLAMINES

[75] Inventors: Elso Manghisi, Monza; Aldo Salimbeni, Milan; Giancarlo Fregnan, Milan, all of Italy

[73] Assignee: Istituto Luso Farmaco d'Italia S.r.l., Milan, Italy

[22] Filed: Jan. 31, 1975

[21] Appl. No.: 545,946

[30] Foreign Application Priority Data
Feb. 5, 1974 Italy .................................. 20199/74
Jan. 14, 1975 Italy .................................. 19264/75

[52] U.S. Cl. ............................ 424/330; 260/240 R; 260/570.7; 260/240 J; 424/248; 424/267; 424/274; 424/250; 260/247.7 S; 260/268 DK; 260/293.8

[51] Int. Cl.² .................... C07C 87/06; A01N 9/20; A01N 9/24

[58] Field of Search ........................ 260/570.7 R

[56] References Cited
UNITED STATES PATENTS
3,105,854  10/1963  Druey et al. ................ 260/570.7 R
3,632,779   1/1972  Marshall ..................... 260/570.7 R FOREIGN PATENTS OR APPLICATIONS
44-27369  11/1969  Japan ............................ 260/570.7

*Primary Examiner*—Allen B. Curtis
*Attorney, Agent, or Firm*—Ladas, Parry, Von Gehr, Goldsmith & Deschamps

[57] ABSTRACT

The invention provides a new class of aminoalkoxyphenoxyalkenones having interesting pharmacological properties.

13 Claims, No Drawings

PHENOXYALKYLAMINES

This invention relates to phenoxyalkylamines and their preparation.

The invention provides the compounds of the formula:

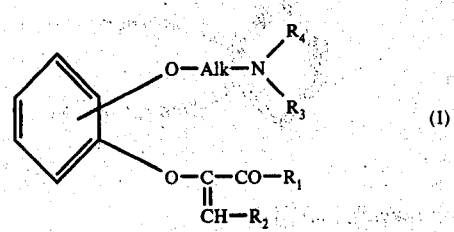

and their stereoisomers and optical isomers, and pharmaceutically acceptable acid addition salts in which the

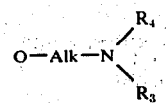

group may be in the ortho, meta or para position, $R_1$ is a linear or branched alkyl of 1 to 4 carbon atoms, such as methyl, ethyl, propyl, or isopropyl, or a monocarbocyclic aryl group such as phenyl, unsubstituted or substituted by one or more halogen atoms (such as fluorine, chlorine, or bromine), or methyl or methoxy groups; $R_2$ is an alkyl group of 1 to 4 carbon atoms such as methyl, or ethyl or a monocarbocyclic aryl group such as phenyl, unsubstituted or substituted by one or more halogen atoms, or alkyls of 1 to 4 carbon atoms, such as methyl or ethyl or methoxy groups; Alk represents a linear or branched alkylene chain of 1 to 4 carbon atoms, such as methylene, ethylene, propylene, or isopropylene, or a hydroxy alkylene chain such as 2-hydroxypropylene, or 3-hydroxybutylene; and $$N\begin{matrix}R_3\\R_4\end{matrix}$$

represents a substituted or unsubstituted amino group in which $R_3$ and $R_4$ which are the same or different, are each hydrogen, alkyl of 1 to 4 carbon atoms each, dialkylaminoalkyl of up to 4 carbon atoms in each alkyl, carbocyclic aryl, particularly phenyl, cycloalkyl of 3 to 8 carbon atoms, carbocyclic arylalkyl, of 1 to 4 carbon atoms in the alkyl, particularly phenyl alkyl; or hydroxy alkyl of up to 4 carbon atoms in which the hydroxyl is separated from the nitrogen by at least two carbon atoms, or the radical $$N\begin{matrix}R_3\\R_4\end{matrix}$$

is an N,N-alkyleneimino group in which the alkylene has 3 to 8 carbon atoms, an N,N-oxo-alkyleneimino in which the alkylene has 4 carbon atoms, an N,N-thioalkyleneimino, in which the alkylene has 4 carbon atoms or N,N-azaalkyleneimino in which the alkylene has 4 to 6 carbon atoms and in which the "aza" nitrogen may be substituted by lower alkyl, lower hydroxyalkyl, lower alkoxyalkyl, lower alkoyloxyalkyl, lower arylalkyl or monocarbocyclic aryl, unsubstituted or substituted by halogen atoms, or lower alkyl, lower alkoxy or nitro groups or by a monocarbocyclic heterocyclic aryl. Thus the group $NR_3R_4$ may be N-alkylamino for example methylamino, ethylamino, propylamino, isopropylamino, or tert-butylamino; N-cycloalkylamino, for example N-cyclohexylamino; N-hydroxyalkylamino for example N-2-hydroxyethylamino, N-[2-hydroxy-2-(3',5'-dihydroxy)-phenyl]-ethylamino, N-[1-methyl-2-hydroxy-2-(4'-hydroxy)-phenyl]-ethylamino; N-arylalkylamino, for example benzylamino; N-dialkylaminoalkylamino for example N,N'-diethylethylenediamino; N-arylamino for example N-phenylamino or substituted N-phenylamino; N,N-dialkylamino for example N,N-dimethylamino, N-methyl-N-ethylamino, N,N-diethylamino, N,N-di-n-propylamino, or N,N-di-isopropylamino; N-cycloalkyl-N-alkylamino in which the cycloalkyl has 3 to 8 atoms for example N-cyclopentyl-N-methylamino, or N-cyclohexyl-N-methylamino; N-lower alkyl-N-phenylalkylamino for example N-benzyl-N-methylamino, or N-ethyl-N-phenylethylamino; N-hydroxyalkyl-N-alkylamino in which the hydroxyl is separated from the nitrogen by at least two carbon atoms, for example N-ethyl-N-(2-hydroxyethyl)-amino; N,N-dihydroxyalkylamino for example N,N-di-(2-hydroxyethyl)-amino; N,N-alkyleneimino in which the alkylene has 3 to 8 carbon atoms, for example 1-pyrrolidino, 1-piperidino, 2-methyl-1-piperidino, 4-hydroxy-4-phenyl-1-piperidino, 4-hydroxy-4-p-chlorophenyl-1-piperidino, 4-carboxamino-4-phenyl-1-piperidino, 4-benzoylamino-1-piperidino, 4-p-fluorobenzoyl-1-piperidino, 1-N,N-(1,6-hexylene)imino, or 1-N,N-(1,7-heptylene)imino; N,N-oxo-alkyleneimino in which the alkylene has preferably 4 carbon atoms, for example 4-morpholino; N,N-thio-alkyleneimino, in which the alkylene has preferably 4 carbon atoms for example 4-thio-morpholino; or N,N-azaalkyleneimino in which the alkylene has 4 to 6 carbon atoms and in which the "aza" nitrogen may be substituted for example by lower alkyl, for example methyl, ethyl, or propyl, lower hydroxyalkyl, for example hydroxyethyl, lower alkoxyalkyl, for example methoxyethyl, lower alkoyloxyalkyl for example acetoxyethyl, lower arylalkyl for example benzyl, diphenylmethyl, 2-phenylethyl, or 2,3'-indolyethyl, or by a monocarbocyclic aryl, preferably phenyl, unsubstituted or substituted by halogen, or alkyl, lower alkoxy or nitro groups for example phenyl, 2-tolyl, 2,3-xylyl, 4-chlorophenyl, or 2-methoxyphenyl, or by a monocarbocyclic heterocyclic aryl for example 2-pyridine, 2-furan, or 2-thiophene, and which may be represented by piperazino, 4-methyl-1-piperazino, 4-ethyl-1-piperazino, 4-(2-hydroxyethyl)-1-piperazino, 4-(2-acetoxyethyl)-1-piperazino, 4-benzyl-1-piperazino, 4-[2'-(3'-indolyl)-ethyl]-1-piperazino, 4-phenyl-1-piperazino, 4-p-chlorophenyl-1-piperazino, 4,2'-methoxyphenyl-1-piperazino, 4-2'-pyridyl-1-piperazino, or 4-3'-pyridyl-1-piperazino.

The acid addition salts of the aforesaid compounds may be with pharmaceutically acceptable inorganic acids for example hydrochloric, hydrobromic, nitric, sulphuric, or phosphoric acid, or with organic carboxylic acids for example acetic, propionic, glycolic, malonic, succinic, maleic, hydryxymaleic, fumaric, malic, tartaric, citric, glucuronic, benzoic, mandelic, salicyclic, 4-aminosalicyclic, 2-phenoxybenzoic, 2-acetoxybenzoic, pamoic, nicotinic, or isonicotinic acid, or with an organic sulphonic acid for example methane sulphonic, ehtane sulphonic, 2-hydroxyethane sulphonic, ethane-1,2-disulphonic, p-toluene-sulphonic, or naphthalene-2-sulphonic acid. Mono or poly salts are formed according to the number of salifiable groups present in the molecules.

In the following description the meaning of the symbols $R_1$, $R_2$, $R_3$, $R_4$, Alk is as given heretofore. The intermediates II, IV, VI may be prepared as described in the Italian Patent Application No. 19858 A/74, filed Jan. 25, 1974 (A/23931).

According to a feature of the invention, the compounds of formula I are made by reacting a compound of formula:

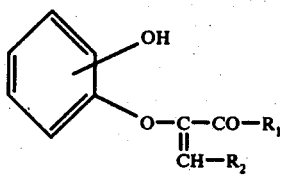

(II)

with a halogeno-alkylamine of the formula:

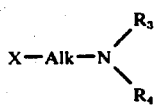

(III)

where X is chlorine or bromine, preferably in the presence of a basic substance such as sodium hydroxide, potassium carbonate, NaH, or $NaNH_2$ and in a solvent such as water, an alcohol, a ketone, an aromatic or aliphatic hydrocarbon, or N,N-dimethylformamide, in general at the boiling point of the reaction solvent.

According to a further feature of the invention, the compounds of formula I are made by reacting a compound of the formula:

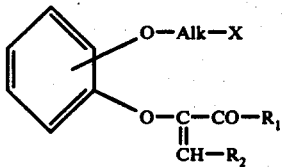

(IV)

where X is chlorine or bromine, with an amine of formula:

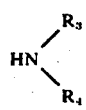

(V)

In general, the operation is carried out in a non-polar solvent such as benzene, toluene, or xylene, at its boiling point using an excess of amine. It is possible however to operate in a hydroxylic solvent such as butanol in the presence of a proton acceptor such as for example potassium carbonate.

Compounds of formula I in which Alk is a hydroxyalkyl chain may be prepared by reacting a compound of formula:

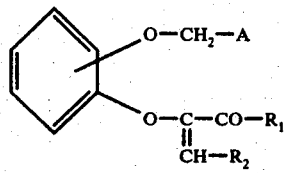

(VI)

in which A may be

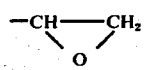

or

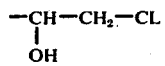

with an amine formula:

(V)

The reaction is preferably carried out in an organic solvent such as acetone, methylethyl ketone, dioxan, or alcohol at boiling point using an excess of amine.

The compounds of formula I and their salts show, according to their substituents, local anaesthetic action, anti-arrhytmic action, action on the central nervous system, action on the adrenergic receptors, hypotensive action and (in some cases) action inhibiting the aggregation of platelets.

They may be administered locally, orally by injection or through the rectum by means of suitable pharmaceutical formulations in solid, liquid or suspension form (e.g. ointments, lotions, tablets, capsules, phials, syrups, or suppositories).

The Tables given hereinafter summarise the pharmacological characteristics of certain compounds described in the present application, identified by the following numbers:

LR 460: 3-[o-(β-N,N-diethylaminoethoxy)-phenoxy]-4-phenyl-3-buten-2one citrate.

LR 527: 3-[o-(γ-piperidino propoxy)-phenoxy]-4-phenyl-3-buten-2-one citrate.

LR 544: 3-[o-(β-morpholinoethoxy)-phenoxy]-4-phenyl-3-buten-2-one hydrochloride.

LR 559: 3-[o-(γ-N,N-dimethylaminopropoxy)-phenoxy]-4-phenyl-3-buten-2-one citrate.

560: 3-[o-(β-piperidinoethoxy)-phenoxy]-4-phenyl-3-buten-2-one hydrochloride monohydrate.

LR 584: 3-[o-(γ-N-tert-butylamino-β-hydroxypropoxy)-phenoxy]-4-phenyl-3-buten-2-one hydrobromide.

LR 589: 1,3-diphenyl-2-[o-(β-,N,N-diethylaminoethoxy)-phenoxy]-2-propen-1-one hydrochloride.

LR 590: 3-[p-(β-N,N-diethylaminoethoxy)-phenoxy]-4-phenyl-3-buten-2-one citrate.

LR 614: 3-[o(γ-N-tert-butylamino-propoxy)-phenoxy) -4-phenyl-3-buten-2-one hydrochloride.

LR 641: 3-[o-(γ-N-methyl-piperazino-propoxy)-phenoxy]-4-phenyl-3-buten-2-one dimaleate.

The anti-arrhythmic activity was evaluated in the rat by the method of Malinow et al. (Rev. Argent. Cardiol. 1952, 19 120), in the isolated rabbit atrium by the Dawes method (Brit. J. Pharmacol. 1946, 1 90), and in the cat heart by electrical stimulation by the Johnson method (Brit. J. Pharmacol. 1954, 9, 341).

The changes in systemic arterial pressure in the cat (anaesthetised with chloralose-urethane) induced by drugs by intravenous administration were recorded by catheterising an artery (generally the carotid) to a pressure transducer able to transmit a signal, suitably amplified, to a printout system.

The anti-aggregation activity on the platelets was evaluated in the rabbit in vitro by the following method. The blood, withdrawn from conscious rabbits, was centrifuged in the presence of sodium citrate (3.8%) at 350 g for 10 minutes, to separate the plasma rich in platelets (PRP) from the rest. The aggregation of the platelets was carried out by bringing the PRP into contact with suitable doses of adenosin sodium diphosphate in the presence of a possible inhibitor or its carrier. The measurement of aggregation was made continuously by the turbidimetric method.

The results obtained are shown in the following table.

and the filtrate is evaporated to dryness. The residue is dissolved in water and extracted a number of times with diethyl ether. The ether phase, after drying over $Na_2SO_4$, is evaporated to dryness and purified by distillation in a bulb apparatus. (B.P. 200°–210°/0.6 mm Hg).

The citrate is prepared from the oil obtained, m.p. 108°–9° C.

The following are similarly prepared:

3-[o-(β-morpholinoethoxy)-phenoxy]-4-phenyl-3-buten-2-one (hydrochloride — m.p. 177°–9° C.);

3-[o-(β-piperidinoethoxy)-phenoxy]-4-phenyl-3-buten-2-one (hydrochloride monohydrate — m.p. 121°–3° C.);

3-[o-(β-pyrrolidinoethoxy)-phenoxy]-4-phenyl-3-buten-2-one (m.p. 54°–5° C.);

1,3-diphenyl-2-[o-(β-N,N-diethylaminoethoxy)-phenoxy]-2-propen-1-one (hydrochloride — m.p. 170°–2° C.); and 3-[p-(β-N,N-diethylaminoethoxy)-phenoxy]-4-phenyl-3-buten-2-one (citrate — m.p. 98°–100° C.).

EXAMPLE 2

3-[o-(γ-piperidinopropoxy)-phenoxy]-4-phenyl-3-buten-2-one 37.5 g of 3-[o-(γ-bromopropoxy)-phenoxy]-4-phenyl-3-buten-2-one and 17 g of piperidine in 300 cc of anhydrous toluene are heated under reflux for 24 hours. After cooling, the mixture is concentrated to one third of its volume, anhydrous ether is added and the precipitated solid is filtered off. The ether phase is evaporated to dryness, and the residue is treated with hexane. The citrate is prepared from the solid obtained, and has a m.p. of 111°–2° C (from isopropyl alcohol-

TABLE

| Substance | Acute toxicity Mouse $LD_{50}$ mg/kg ip. | Acute toxicity Rat $LD_{50}$ mg/kg iv | Anti-arrhythmic activity $CaCl_2$ anaesthetised rat $ED_{50}$* mg/kg iv | Anti-arrhythmic activity Electrical stimulation isolated atrium rabbit $ED_{30}$ mcg/ml | Hypotensive activity, anaesthetised cat $ED_{30}$ mg/kg iv | Platelet anti-aggregation activity in rabbit, in vitro $ED_{50}$ mg/ml |
|---|---|---|---|---|---|---|
| LR 460 | 75.0 | 8.9 | 0.37 (24) | 0.68 | 2.00 | Φ |
| LR 527 | 62.0 | 6.5 | 0.20 (32) | 1.60 | 1.90 | 0.10 |
| LR 544 | 180.0 | 50.0 | 5.0 (10) | 6.00 | 10.00 | Φ |
| LR 559 | 110.0 | 13.5 | 0.37 (36) | 3.00 | 1.25 | Φ |
| LR 560 | 62.5 | 11.2 | 0.75 (15) | 3.00 | 5.00 | Φ |
| LR 584 | 80.0 | 19.0 | 1.90 (10) | 0.50 | 1.30 | 0.03 |
| LR 589 | 125.0 | 22.4 | 1.40 (16) | 2.80 | 10.00 | 0.30 |
| LR 590 | 190.0 | 22.2 | 1.50 (15) | 2.30 | 5.00 | 0.30 |
| LR 614 | 62.5 | 12.5 | 1.50 (8) | 2.30 | 5.00 | 0.03 |
| LR 641 | 125.0 | 23.9 | 2.50 (10) | 1.30 | 10.00 | 0.20 |
| Quinidine | 176.0 | 48.0 | 4.70 (10) | 5.10 | 5.00 | 0.60 |

*The therapeutic index obtained from the ratio $DL_{50}$ rat iv/$DE_{50}$ is given in parentheses
Φ inactive The following Examples illustrate the invention. The melting and boiling points have not been corrected. The identity of the substances and their purity have been ascertained by elementary analysis of C, H, N (and halogens were present), infrared, N.M.R. and U.V. spectra.

EXAMPLE 1

3-[o-(β-N,N-diethylaminoethoxy)-phenoxy]-4-phenyl-3-buten-2-one 21 g of N,N-diethylaminoethyl chloride are added drop by drop to 35 g of the sodium salt of 3-o-hydroxy-phenoxy-4-phenyl-3-butene-2-one suspended in 600 cc of anhydrous acetone. The mixture is heated under reflux for 4 hours, the sodium chloride is filtered off, ether).

The following are similarly prepared:

3-[o-(γ-N,N-dimethylaminopropoxy)-phenoxy]-4-phenyl-3-buten-2-one (citrate — m.p. 99°–101° C.);

3-[o-(γ-N-tert-butylaminopropoxy)-phenoxy]-4-phenyl-3-buten-2-one (hydrochloride — m.p. 175°–7° C from absolute alcohol);

3-[o-(γ-N-methyl-piperazino propoxy)-phenoxy]-4-phenyl-3-buten-2-one (dimaleate — m.p. 187°–9° C from 95% alcohol); and 3-[o-(γ-N-phenylpiperazinopropoxy)-phenoxy]-4-phenyl-3-buten-2-one (dihydrochloride — m.p. 160°–1° C from absolute alcohol).

By using 3-[p-(γ-bromopropoxy)-phenoxy]-4-phenyl-3-buten-2-one as the starting material, the following may likewise be obtained:

3-[p-(y-N-methylamino-propoxy)-phenoxy]-4-phenyl-3-buten-2-one (oxalate — m.p. 105°–107° C from isopropyl alcohol); and 3-[p-(y-N-4'-p-chlorophenyl-4'-hydroxypiperidino-propoxy)-phenoxy]-4-phenyl-3-buten-2-one (m.p. 142°–4° from EtOH).

EXAMPLE 3

3-[o-(y-N-tert-butylamino-β-hydroxypropoxy)-phenoxy]-4-phenyl-3-buten-one 10 g of 3-[o-(2,3-epoxypropoxy)-phenoxy]-4-phenyl-3-buten-2-one and 100 cc of tert-butylamine are heated under reflux for 12 hours. The excess amine is eliminated under vacuum. From the residual oil, purified by distillation in a bulb apparatus, the hydrobromide is prepared, m.p. 155°–6° C (from alcohol-ether).

EXAMPLE 4

3-[p-β-methyl-β-N,N-dimethylamino-ethoxy-phenoxy]-4-phenyl-3-buten-2-one 3,2 g of β-methyl-β-N,N-diethylaminoethylchloride are added to 5 g of 3-p-hyroxyphenoxy-4-phenyl-3-buten-2-one, 3,8 g of $K_2CO_3$ and 500 cc of anhydrous acetone. The mixture is heated under reflux for 24 hours and then filtered and evaporated to dryness. The residue is dissolved in ether and the ether solution is washed with dilute NaOH solution. After drying over $Na_2SO_4$, the solvent is eliminated under vacuum. The oil obtained is purified by distillation in a bulb apparatus. b.p. 230°–50° C/0.5 mm.Hg.

The following is similarly prepared:

3-[p-(β-N,N-diethylaminoethoxy)-phenoxy]-4-p-chlorophenyl-3-butene-2-one (citrate m.p. 119°–120° C from alcohol-ether).

EXAMPLE 5

3-[p-(γ-N-tert-butylamino-β-hydroxypropoxy)-phenoxy]-4-phenyl-3-buten-2-one 10 g of 3-[p-(2,3-epoxypropoxy)-phenoxy]-4-phenyl-3-buten-2-one and 100 cc of tert-butylamine are heated under reflux for 12 hours. Excess amine is eliminated under vacuum and the process is completed as in Example 3 (oxalate m.p. 149°–151° C from isopropyl alcohol).

We claim:
1. A phenoxyalkylamine of the formula:

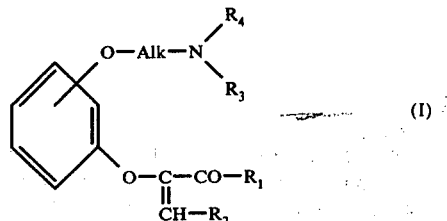

and its stereoisomers and optical isomers, and pharmaceutically acceptable acid addition salts, in which the

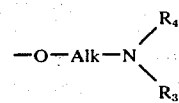

group may be in the ortho, meta or para position, $R_1$ is a linear or branched alkyl of 1 to 4 carbon atoms, or a monocarbocyclic aryl group, unsubstituted or substituted by one or more halogen atoms, or methyl or methoxy grups; $R_2$ is an alkyl of 1 to 4 carbon atoms or a monocarbocyclic aryl group unsubstituted or substituted by one or more halogen atoms, or alkyls of 1 to 4 carbon atoms, or methoxy groups; Alk is a linear or branched alkylene chain of 1 to 4 carbon atoms, or a hydroxy alkylene chain; and $R_3$ and $R_4$, which are the same or different, are each hydrogen, alkyl of 1 to 4 carbon atoms each, dialkylaminoalkyl of up to 4 carbon atoms in each alkyl, carbocyclic aryl, cycloalkyl of 3 to 8 carbon atoms, carbocyclic arylalkyl of 1 to 4 carbon atoms in the alkyl, or hydroxyalkyl of up to 4 carbon atoms in which the hydroxyl is separated from the nitrogen by at least two carbon atoms.

2. A phenoxyalkylamine according to claim 1 and its pharmaceutically acceptable acid addition salts in which the $$-O-Alk-N\begin{matrix}R_4\\ \\R_3\end{matrix}$$

group is in the ortho or para position, $R_1$ is methyl or phenyl, $R_2$ is phenyl or 4-chlorophenyl, Alk is ethylene, propylene, isopropylene or hydroxypropylene, and $R_3$ and $R_4$ are each hydrogen, methyl, ethyl, tert-butyl.

3. A phenoxyalkylamine of claim 1 comprising 3-[o-(β-N,N-Diethylaminoethoxy)-phenoxy]-4-phenyl-3-buten-2-one, and its pharmaceutically acceptable acid addition salts.

4. A phenoxyalkylamine of claim 1 comprising 1,3-Diphenyl-2-[o-(β-N,N-diethylaminoethoxy)-phenoxy]-2-propen-1-one, and its pharmaceutically acceptable acid addition salts.

5. A phenoxyalkylamine of claim 1 comprising 3-[p-(β-N,N-Di-ethylaminoethoxy)-phenoxy]-4-phenyl-3-buten-2-one, and its pharmaceutically acceptable acid addition salts.

6. A phenoxyalkylamine of claim 1 comprising 3-[o-(y-N,N-Dimethylaminopropoxy)-phenoxy]-4-phenyl-3-buten-2one, and its pharamaceutically acceptable acid addition salts.

7. A phenoxyalkylamine of claim 1 comprising 3-[o-(y-N-tert-Butylamino-β-hydroxy-propoxy)phenoxy]-4-phenyl-3-buten-2-one, and its pharmaceutically acceptable acid addition salts.

8. A phenoxyalkylamine of claim 1 comprising 3-[o-(y-N-tert-Butylamino propoxy)-phenoxy]-4-phenyl-3-buten-2-one, and its pharmaceutically acceptable acid addition salts.

9. A phenoxyalkylamine of claim 1 comprising 3-[p-(y-N-Methylamino propoxy)-phenoxy]-4-phenyl-3-buten-2-one, and its pharamaceutically acceptable acid addition salts.

10. A phenoxyalkylamine of claim 1 comprising 3-[p-(β-Methyl-β-N,N-dimethylamino ethoxy)-phenoxy]-4-phenyl-3-buten-2-one, and its pharmaceutically acceptable acid addition salts.

11. A phenoxyalkylamine of claim 1 comprising 3-[p-(γ-N-tert-Butylamino-β-hydroxy propoxy)-phenoxy]-4-phenyl-3-buten-2-one, and its pharmaceutically acceptable acid addition salts.

12. A phenoxyalkylamine of claim 1 comprising 3-[p-(β-N,N-Diethylamino ethoxy)-phenoxy]-4-p-chlorophenyl-3-buten-2-one, and its pharmaceutically acceptable acid addition salts.

13. A pharmaceutical composition comprising as active principle one or more compounds as claimed in claim 1, in the form of free base or pharmaceutically acceptable salt, in association with a significant amount of pharmaceutically acceptable and compatible carrier.

* * * * *